(12) United States Patent
Suda (10) Patent No.: US 9,033,865 B2
(45) Date of Patent: May 19, 2015

(54) TREATMENT TOOL FOR ENDOSCOPE (75) Inventor: Naoto Suda, Hanno (JP)

(73) Assignee: OLYMPUS MEDICAL SYSTEMS CORP. (JP)

(*) Notice: Subject to any disclaimer, the term of this patent is extended or adjusted under 35 U.S.C. 154(b) by 1856 days.

(21) Appl. No.: 12/133,924

(22) Filed: Jun. 5, 2008

(65) Prior Publication Data

US 2008/0242925 A1 Oct. 2, 2008

Related U.S. Application Data (63) Continuation of application No. PCT/JP2006/324737, filed on Dec. 12, 2006.

(30) Foreign Application Priority Data

Dec. 13, 2005 (JP) .................................. 2005-358561

(51) Int. Cl.
| | | |
|---|---|---|
| *A61B 1/00* | (2006.01) | |
| *A61B 1/04* | (2006.01) | |
| *A61M 5/178* | (2006.01) | |
| *A61B 17/00* | (2006.01) | |
| *A61B 10/04* | (2006.01) | |

(Continued)

(52) U.S. Cl.
CPC ............. *A61B 10/04* (2013.01); *A61B 1/00128* (2013.01); *A61B 1/00137* (2013.01); *A61B 1/018* (2013.01); *A61B 1/313* (2013.01); *A61B 10/06* (2013.01); *A61B 19/38* (2013.01); *A61B 2010/045* (2013.01); *A61B 2017/00477* (2013.01)

(58) Field of Classification Search
USPC ......... 600/101, 102, 104, 106, 107, 114–116, 600/123, 125, 153, 154; 606/205–209, 167, 606/170, 172; 604/167.01–167.07
See application file for complete search history.

(56) References Cited

U.S. PATENT DOCUMENTS

| | | | |
|---|---|---|---|
| 5,167,636 A | 12/1992 | Clement | |
| 5,601,533 A | 2/1997 | Hancke et al. | |

(Continued)

FOREIGN PATENT DOCUMENTS

| | | |
|---|---|---|
| JP | 55-70108 | 5/1980 |
| JP | 07-178098 | 7/1995 |

(Continued)

OTHER PUBLICATIONS

Extended European Search Report dated Oct. 7, 2009 in corresponding European Patent Application No. EP 06 83 4492 (in English language).

(Continued)

*Primary Examiner* — Ryan Henderson
(74) *Attorney, Agent, or Firm* — Ostrolenk Faber LLP (57) ABSTRACT

A treatment tool for an endoscope including: an insertion section inserted from a mouth ring provided at the base-end portion of a channel of the endoscope to the inside of the channel; an operation section provided at the base end of the insertion section; a rigid guide member having a tubular shape, externally fitted around the insertion section at the base end of the insertion section, and fixed to the operation section; and a fixing section that is externally fitted around the guide member, firmly attaches between the inner wall of the mouth ring or the channel and the guide member, and fixes the guide member to the inner wall of the mouth ring or the channel.

3 Claims, 11 Drawing Sheets

(51) Int. Cl.
*A61B 1/018* (2006.01)
*A61B 1/313* (2006.01)
*A61B 10/06* (2006.01)
*A61B 19/00* (2006.01)

(56) References Cited

U.S. PATENT DOCUMENTS

| | | | |
|---|---|---|---|
| 5,855,569 A | 1/1999 | Komi | |
| 2001/0021825 A1* | 9/2001 | Becker et al. | 604/167.01 |
| 2003/0195388 A1* | 10/2003 | Niwa et al. | 600/117 |

FOREIGN PATENT DOCUMENTS

| | | | | |
|---|---|---|---|---|
| JP | 2001-275947 | | 10/2001 | |
| JP | 2004-248770 | | 9/2004 | |
| JP | 2005-137814 | | 6/2005 | |
| JP | 2005137454 A | * | 6/2005 | ............... A61B 1/00 |

OTHER PUBLICATIONS

International Search Report dated Jan. 9, 2007 issued in corresponding PCT Application No. PCT/JP2006/324737.

* cited by examiner

TREATMENT TOOL FOR ENDOSCOPE

BACKGROUND OF THE INVENTION

1. Field of the Invention

The present invention relates to a treatment tool for an endoscope that is inserted into a body from a channel of the endoscope, extracts cells and tissue at a predetermined region in the body, and performs excision and the like.

Priority is claimed on Japanese Patent Application No. 2005-358561, filed Dec. 13, 2005, the content of which is incorporated herein by reference.

2. Description of Related Art

A treatment tool for an endoscope is used by insertion inside a channel of an endoscope insertion section that has been inserted into a body and protruding/retracting the treatment section from the distal end of the endoscope insertion section.

The endoscope channel is continuous for passage from the distal end of the endoscope insertion section that is positioned in the body to an insertion opening outside of the body at which the endoscope treatment device is inserted.

That is, the endoscope channel is put in the state of making continuous the space at a predetermined region in the body and external space.

In the case of performing observation of a predetermined region with an endoscope and in the case of performing treatment of a predetermined region with the treatment tool for an endoscope, it is necessary to make the air pressure in the body higher than the atmospheric pressure in order to secure the space around the predetermined area.

However, in such a case, bodily fluids and the like in the body may flow backwards through the channel due to the atmospheric-pressure difference of the inside of the body and the outside of the body.

For this reason, a forceps plug formed with rubber or the like is provided at the mouth ring provided at the insertion opening.

A through hole is formed in the center of the forceps plug, and a backflow valve is provided in the through hole.

Due to the back flow valve, the inside of the channel and the inside of the body are separated from the external space.

Also, it is possible to use the treatment tool for an endoscope by inserting the insertion section with a treatment section provided at the distal end from the through hole of the forceps plug into the channel.

As disclosed in Japanese Unexamined Patent Application, First Publication No. H07-178098, as a treatment tool for an endoscope that samples cells and tissue of a predetermined region in a body, a tool for an endoscope is used that is provided with a sheath that has flexibility, an operation section that is provided at the base-end portion of the sheath, a needle tube that is inserted inside the sheath, and a stylet that is inserted inside the needle tube.

In this kind of treatment tool for an endoscope, it is possible to relatively move forward/backward the needle tube and stylet with respect to the sheath by the operation section.

This kind of treatment tool for an endoscope is used by fixing the operation section to a screw that is formed in a mouth ring since accurate operation is required at the predetermined region in the body.

SUMMARY OF THE INVENTION

The treatment tool for an endoscope of the invention includes: an insertion section inserted from a mouth ring provided at a base-end portion of a channel of the endoscope to an inside of the channel; an operation section provided at a base end of the insertion section; a guide member that has a tubular shape, that is externally fitted around the insertion section at the base end of the insertion section, that is fixed to the operation section, and that is rigid; and a fixing section that is externally fitted around the guide member, firmly attaches between an inner wall of the mouth ring or the channel and the guide member, and fixes the guide member to the inner wall of the mouth ring or the channel.

Also, it is preferable that, in the abovementioned treatment tool for an endoscope, the fixing section have a fixing member that is externally fitted around the guide member, that deforms in a radial direction, and that is capable of pressing the inner wall of the mouth ring or the channel.

In the invention, "radial direction" means a direction that intersects the extending direction of a predetermined axis and that radiates.

Accordingly, the radial direction of the fixing member means a direction that intersects the direction along which the axis of the fixing member extends and that radiates.

Also, it is preferable that the abovementioned treatment tool for an endoscope further include: a locking section that is formed at the guide member at a position which is closer to the distal-end side than the position of the fixing member, and that protrudes distally from an axial direction and in the radial direction. In the treatment tool for an endoscope, the fixing section has a pressing member that has a tubular shape, that is externally fitted around the guide member to be capable of moving back and forth in the axial direction, and that is elastically deformable in the radial direction by being sandwiched between the fixing member and the locking section of the guide member and by pressing the fixing member.

Also, it is preferable that the abovementioned treatment tool for an endoscope further include: a tapered section formed at the guide member at a position which is closer to the distal-end side than the position of the fixing member, whose diameter is greater at a distal-end side than at a base-end side. In the treatment tool for an endoscope, the fixing section has a pressing member of a tubular shape that is externally fitted around the guide member to be capable of moving back and forth in an axial direction, and that is elastically expandable in diameter by causing the fixing member fixed at the distal-end portion to be disposed at the tapered section.

Also, it is preferable that the abovementioned treatment tool for an endoscope further include: a positioning mechanism that is capable of moving the pressing member back and forth in the axial direction and locking the pressing member at a fixed position that causes the fixing member to deform in the radial direction and press the inner wall of the mouth ring or the channel.

Also, it is preferable that, in the abovementioned treatment tool for an endoscope, the insertion section include: a sheath that has flexibility; a needle tube with a tubular shape that is inserted inside the sheath and having a distal-end portion that is sharpened; and a stylet that is passed through the needle tube. In the treatment tool for an endoscope, the operation section has a slider that is capable of moving the needle tube and the stylet back and forth in the axial direction relative to the sheath.

DESCRIPTION OF THE PREFERRED EMBODIMENT

First Embodiment

FIGS. 1 to 5 show a first embodiment of the invention.

Figure 1:
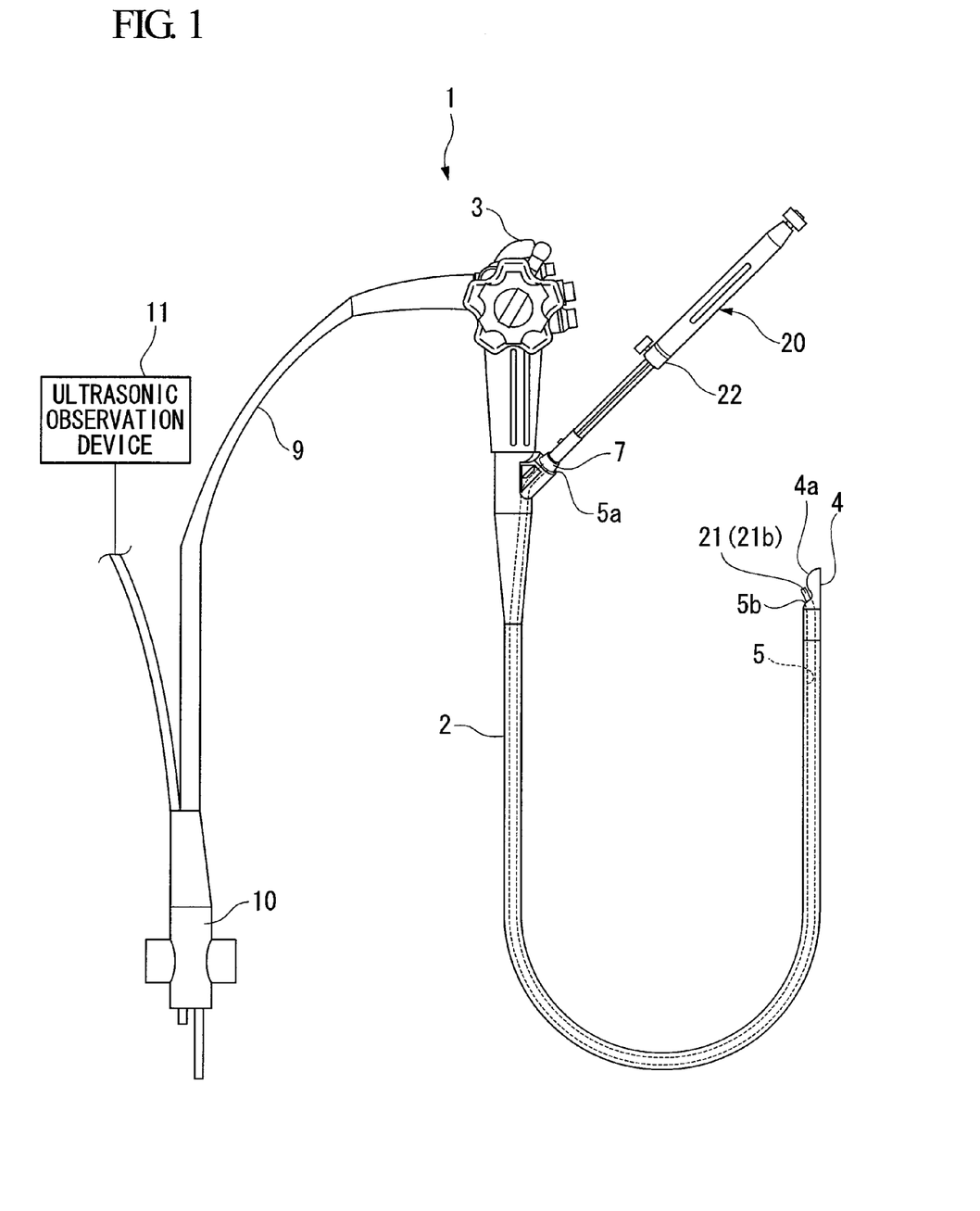
FIG. 1 is an overall view of an ultrasonic endoscope of a first embodiment of the invention.

As shown in FIG. 1, an ultrasonic endoscope 1 has an endoscope insertion section 2 that is inserted into a living body, and an endoscope operation section 3 that is provided at the base end of the endoscope insertion section 2.

The endoscope insertion section 2 has flexibility, and the distal-end side freely curves by operation of the endoscope operation section 3.

A rigid endoscope distal-end portion 4 is formed at the distal end of the endoscope insertion section 2.

Also, the ultrasonic endoscope 1 is provided with a channel 5 that is continuous from an insertion opening 5a of the endoscope operation section 3 to a channel opening portion 5b of the endoscope distal-end portion 4 via the endoscope insertion section 2.

Figure 2:
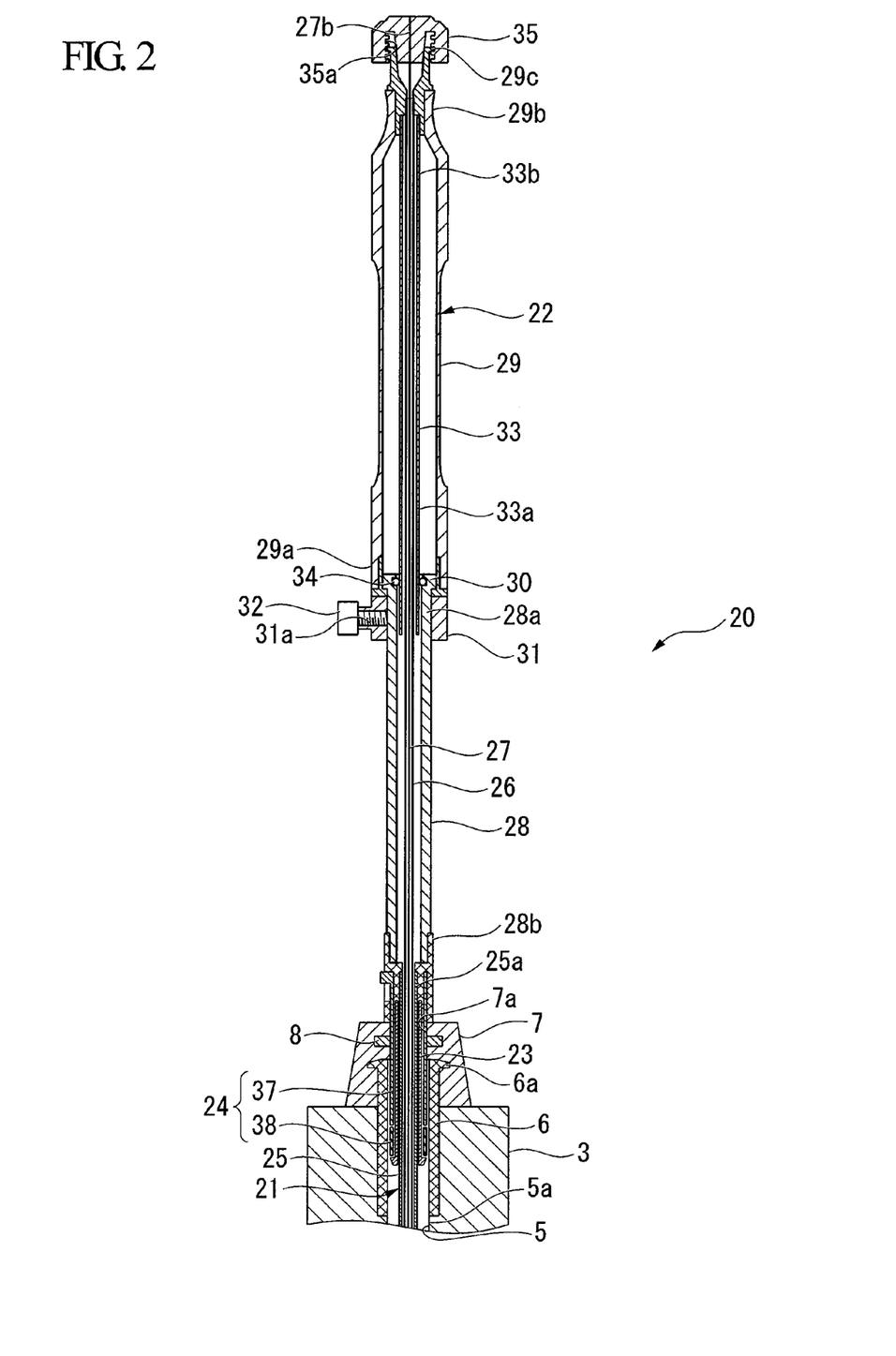
FIG. 2 is a cross-sectional view of the vicinity of the channel insertion opening of the ultrasonic endoscope of the first embodiment of the invention.

FIG. 2 shows a cross-sectional view of the vicinity of the channel insertion opening 5a of the channel 5 of the ultrasonic endoscope 1.

As shown in FIG. 2, a mouth ring 6 that is continuous with the channel 5 is provided at the insertion opening 5a.

A male thread 6a is formed at the distal-end portion of the mouth ring 6.

In addition, a forceps plug 7 is provided at the mouth ring 6.

The forceps plug 7 is made of rubber, fits on the mouth ring 6, and plugs the opening of the mouth ring 6.

A seal 8 is provided on the forceps plug 7.

A through hole 7a is formed in the seal 8, communicates with the mouth ring 6 and the channel 5, and is expandable in the radial direction.

The seal 8 blocks the through hole 7a, and thereby the inside of the channel 5 and the exterior space can be separated.

As shown in FIG. 1, an optical observation section (not illustrated), and an illumination section (not illustrated) are further provided in the interior of the endoscope insertion section 2 and the endoscope distal-end portion 4.

Also, an ultrasonic observation section that has an ultrasonic vibrator section in which a plurality of piezoelectric elements is arranged in the shape of an array is provided on a surface 4a of the endoscope distal-end portion 4.

These are connected to the endoscope operation section 3, enabling optical observation of the area around the endoscope distal-end portion 4 by the optical observation section and the illumination section.

Also, it is possible to transmit and receive ultrasonic waves by the ultrasonic observation section, and to observe the area of the endoscope distal-end portion 4 by the result.

As a result, it is possible to perform visual observation by an ultrasonic observation device 11, by connection from the cable 9 that is connected to the endoscope operation section 3 to the ultrasonic observation device 11 via the connector 10.

Figure 3:
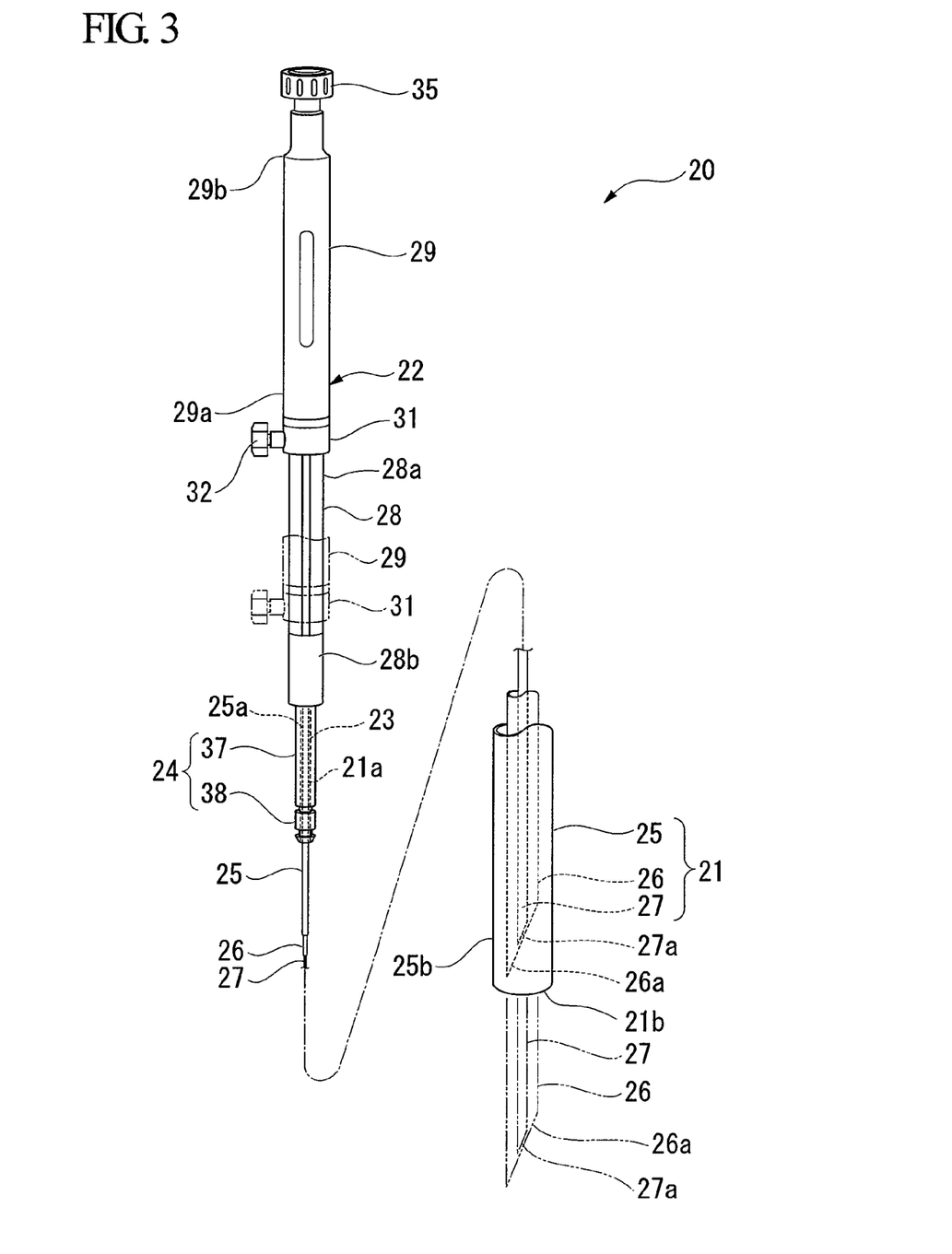
FIG. 3 is an overall view of the puncture needle for an endoscope of the first embodiment of the invention.

As shown in FIG. 3, a puncture needle 20 for the endoscope that is a treatment tool for the endoscope is provided with an insertion section 21 that is inserted inside the channel 5 and an operation section 22 that is provided at a base end 21a of the insertion section 21.

As shown in FIG. 2, the operation section 22 is provided with an operation section body 28 having a substantially tubular shape and a slider 29 having a substantially tubular shape.

The slider 29 is externally fitted around the operation section body 28, and is capable of moving back and forth in the axial direction.

A flange portion 30 that projects in the outer circumferential direction is formed at a base-end portion 28a of the operation section body 28.

The inner diameter of the slider 29 is set to be substantially equal to the outer diameter of the flange portion 30.

Also, a stopper member 31 is provided at a distal-end portion 29a of the slider 29.

The inner diameter of the stopper member 31 is set to be substantially equal to the outer diameter of the operation section body 28.

A screw hole 31a is formed in the stopper member 31, passing through the radial direction thereof, and a fixing screw 32 is screwed therein.

That is, a constitution is provided in which the slider 29 is externally fitted around the operation section body 28 and capable of moving back and forth in the axial direction, with the stopper member 31 abutting the flange portion 30 on the base-end side so that it does not fall out.

Also, the fixing screw 32 is tightened and made to abut the outer circumferential surface of the operation section body 28. It is thereby possible to fix the slider 29 to the operation section body 28 at a predetermined position.

Also, a suction mouthpiece member 29b is provided at the base-end portion opening of the slider 29.

A male thread 29c is formed on the outer circumferential side of the suction mouthpiece member 29b, and a stylet mouthpiece member 35 with a corresponding female thread 35a formed on the inner circumferential side screwed thereon.

The opening of the suction mouthpiece member 29b of the slider 29 is thereby blocked.

A guide pipe 33 is routed inside of the slider 29.

An O-ring 34 that is provided on the inner circumferential side of the operation section body 28 is externally fitted in an airtight manner around the distal-end portion 33a.

Also, a base-end portion 33b of the guide pipe 33 is fixed to the suction mouthpiece member 29b of the slider 29.

Also, as shown in FIGS. 2 and 3, the insertion section 21 is provided with a sheath 25 having a substantially tubular shape, a needle tube 26 having a substantially tubular shape, and a stylet 27 having a substantially bar shape.

The sheath 25 has flexibility.

The needle tube 26 has a distal-end portion 26a that is sharpened and is inserted in the sheath 25.

The stylet 27 has a distal-end portion 27a that is sharpened and is inserted in the needle tube 26.

The sheath 25 is fixed to a connection member 28b having a substantially tubular shape that is provided at the base-end portion of the operation section body 28 at the base-end portion 25a, and communicates with the inside of the operation section body 28.

The needle tube 26 is inserted in the sheath 25, the operation section body 28, and the guide pipe 33 of the slider 29, and is fixed to the suction mouthpiece member 29b.

Moreover, the stylet 27 is inserted in the needle tube 26, and is fixed to the stylet mouthpiece member 35.

That is, as shown in FIG. 3, by moving the slider 29 back and forth in the axial direction on the operation section body 28, the needle tube 26 and the stylet 27 are, along with the slider 29, moved back and forth relative to the sheath 25, and can be protruded and retracted from the distal-end portion 25b of the sheath 25.

Also, by screwing in the fixing screw 32, it is possible to adjust the projection amount of the needle tube 26 and the stylet 27 from the sheath 25.

Moreover, by removing the stylet mouthpiece member 35 in this state, the stylet 27 is drawn out from the needle tube 26.

Then, when a suction device (not illustrated) is connected to the suction mouthpiece member 29b of the slider 29, it is possible to suction cells or tissue and the like of the distal-end portion 26a of the needle tube 26.

The needle tube 26 and the stylet 27 are capable of curving in accordance with the channel 5 along with the sheath 25, and possess rigidity to be capable of piercing a predetermined region in the body.

Figure 4:
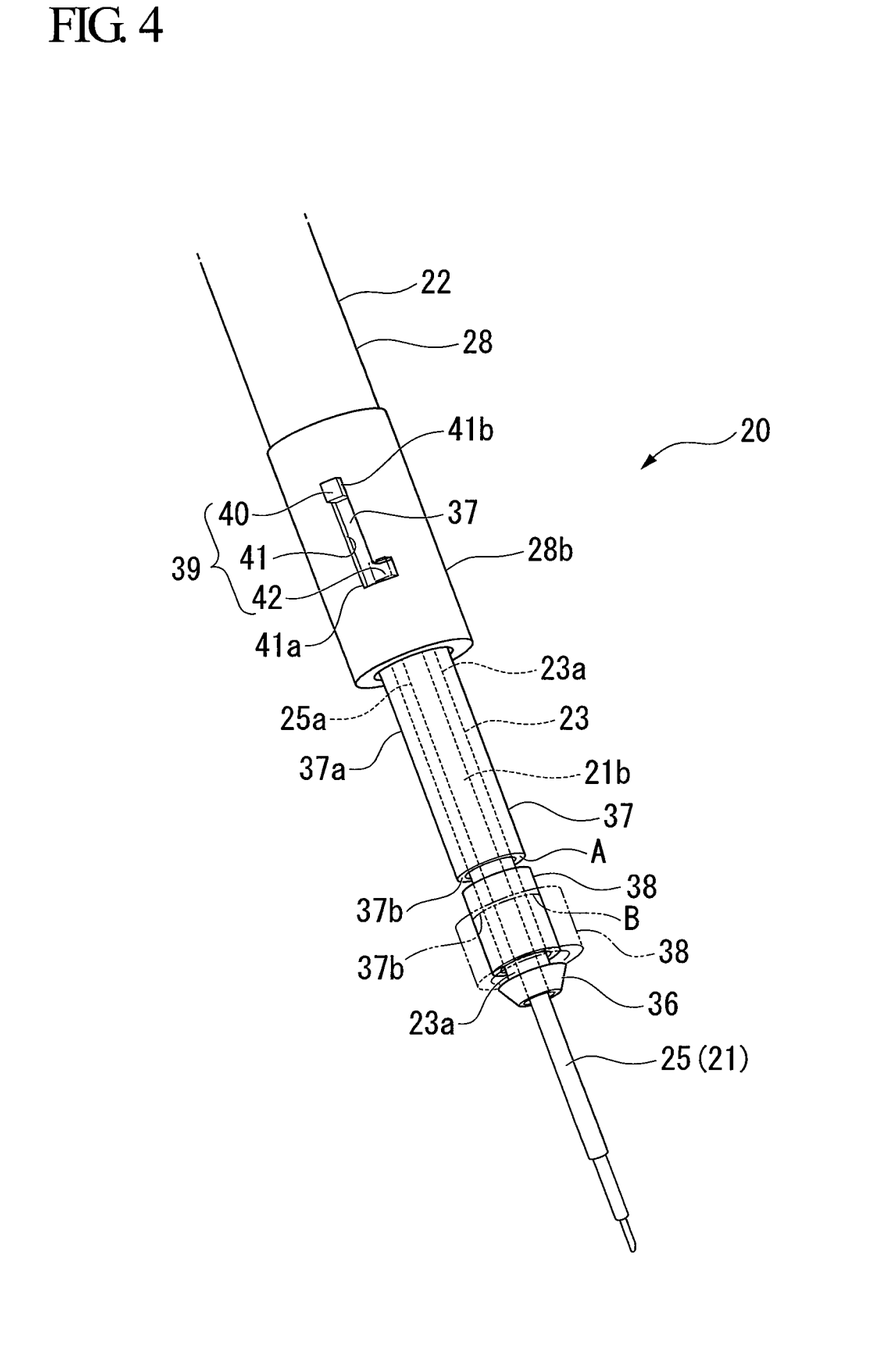
FIG. 4 is an enlarged perspective view of the base-end portion of the insertion section of the puncture needle for an endoscope of the first embodiment of the invention.

FIG. 4 shows a base-end portion of the insertion section 21 of the puncture needle 20 for the endoscope.

Figure 5:
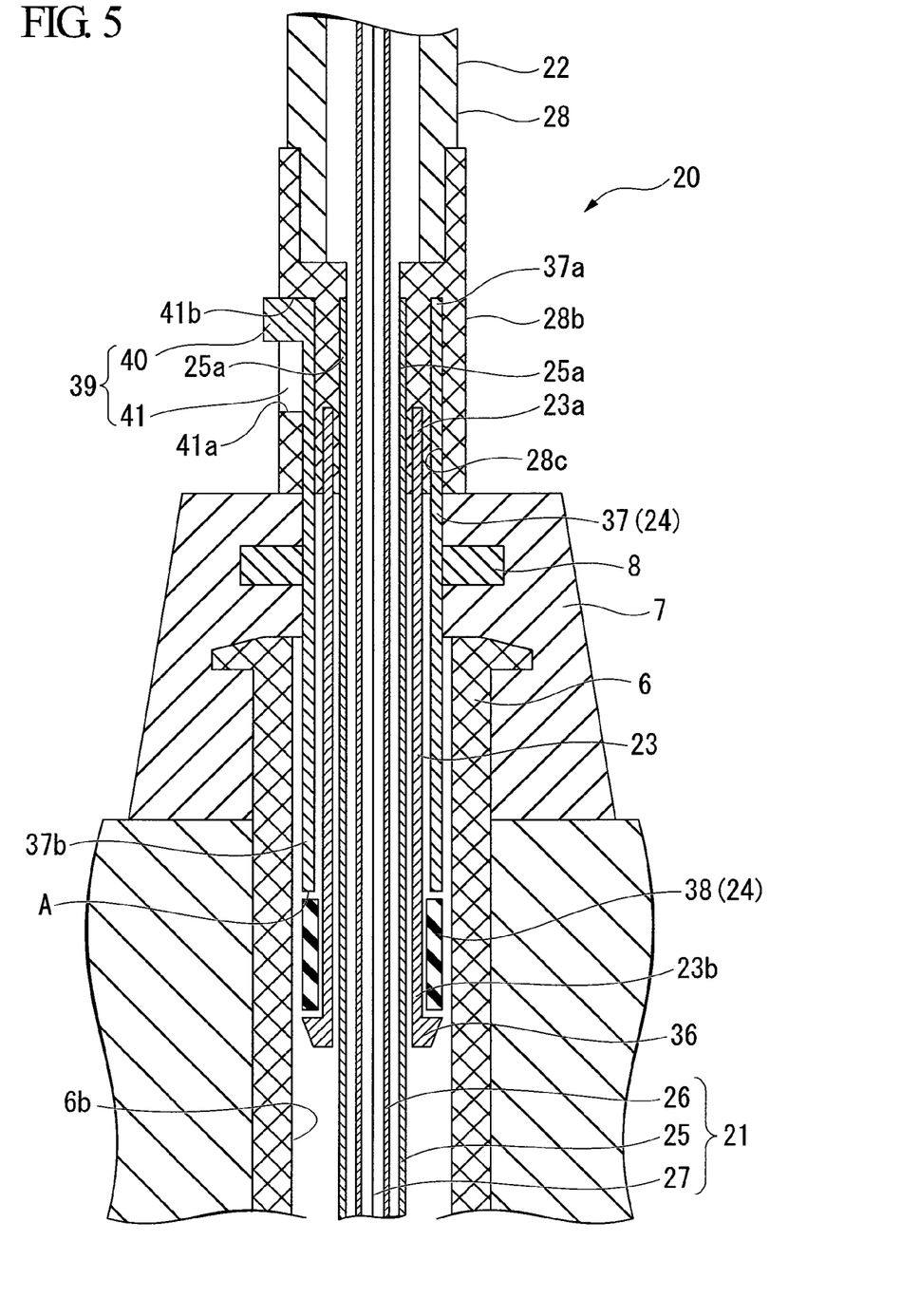
FIG. 5 is an enlarged cross-sectional view of the base-end portion of the insertion section of the puncture needle for an endoscope of the first embodiment of the invention.

Also, FIG. 5 shows an enlarged cross-sectional view of the base-end portion when the insertion section 21 of the puncture needle 20 is inserted in the channel 5.

As shown in FIGS. 4 and 5, the puncture needle 20 is further provided with a guide member 23 having a substantially tubular shape and a fixing section 24 that is externally fitted around the guide member 23.

The guide member 23 has a base-end portion 23a that is fixed to the connection member 28b, and is externally fitted around the insertion section 21.

Also, a locking section 36 that circularly protrudes distally from an axial direction and in the radial direction is formed at the distal portion 23b.

The guide member 23 is made of a rigid material.

Also, the fixing section 24 is constituted by a pressing member 37 having a substantially tubular shape and an elastic member 38 that is a fixing member.

The pressing member 37 has a base-end portion 37a that is fitted in an annular groove 28c that is formed in the connection member 28b, and by being externally fitted around the guide member 23, is capable of moving back and forth in the axial direction.

Also, the elastic member 38 is held between the pressing member 37 and the locking section 36, and externally fitted around the guide member 23.

The pressing member 37 is formed with a rigid material, and the elastic member 38 is formed with rubber, silicone resin, and the like to be capable of elastic deformation.

Moreover, as shown in FIGS. 4 and 5, a positioning mechanism 39 is formed in the connection member 28b and the pressing member 37.

The positioning mechanism 39 is capable of moving the pressing member 37 back and forth in the axial direction in a predetermined range and locking a position in the axial direction of the pressing member 37 at a fixed position B described below.

The positioning mechanism 39 is constituted by a locking projection portion 40, a slot 41, and a notch 42.

The locking projection portion 40 protrudes outward in the radial direction at the base-end portion 37a of the pressing member 37.

The slot 41 is formed lengthwise in the axial direction at the outer periphery side of the connection member 28b.

The notch 42 is formed in the circumferential direction of the connection member 28b at the distal-end portion 41a of the slot 41.

The slot 41 passes through to the fitting groove 28c, and the locking projection portion 40 is fitted therein.

The width of the slot 41 and the notch 42 is set to a width corresponding with the locking projection portion 40.

For this reason, it is possible for the locking projection portion 40 to move back and forth in the axial direction through the slot 41 corresponding to the pressing member 37 moving back and forth in the axial direction.

The set position of a base-end portion 41b of the slot 41 corresponds with the position at which a distal-end portion 37b of the pressing member 37 is retracted (retracted position A).

That is, when the locking projection portion 40 is positioned at the base-end portion 41b of the slot 41, the distal-end portion 37b of the pressing member 37 is positioned at the retracted position A without abutting the elastic member 38.

On the other hand, the set position of a distal-end portion 41a of the slot 41 corresponds with the position of the pressing member 37 that causes the elastic member 38 to deform in the radial direction (fixed position B).

That is, when the locking projection portion 40 is positioned at the distal-end portion 41a of the slot 41, the distal-end portion 37b of the pressing member 37 is positioned at the fixed position B to press the elastic member 38 between the distal-end portion 37b and the locking section 36, causing the elastic member 38 to deform in the radial direction.

Next, the action of the puncture needle 20 for the endoscope shall be described.

First, as shown in FIG. 5, the insertion section 21 is inserted inside of the channel 5 from the mouth ring 6 assuming the pressing member 37 is at the retracted position A.

Since the pressing member 37 is at the retracted position A, and the elastic member 38 is not pressed and is not deformed in the radial direction, it is possible to readily perform insertion with the seal 8 of the forceps plug 7 elastically expanded in diameter to the outer side. Then, it is inserted until the connection member 28b abuts the forceps plug 7.

Next, as shown in FIG. 4, the locking projection portion 40 of the positioning mechanism 39 is moved in the axial direction from the base-end portion 41b of the slot 41 to the distal-end portion 41a, and moreover, is moved in the circumferential direction to be engaged with the notch 42.

Figure 6:
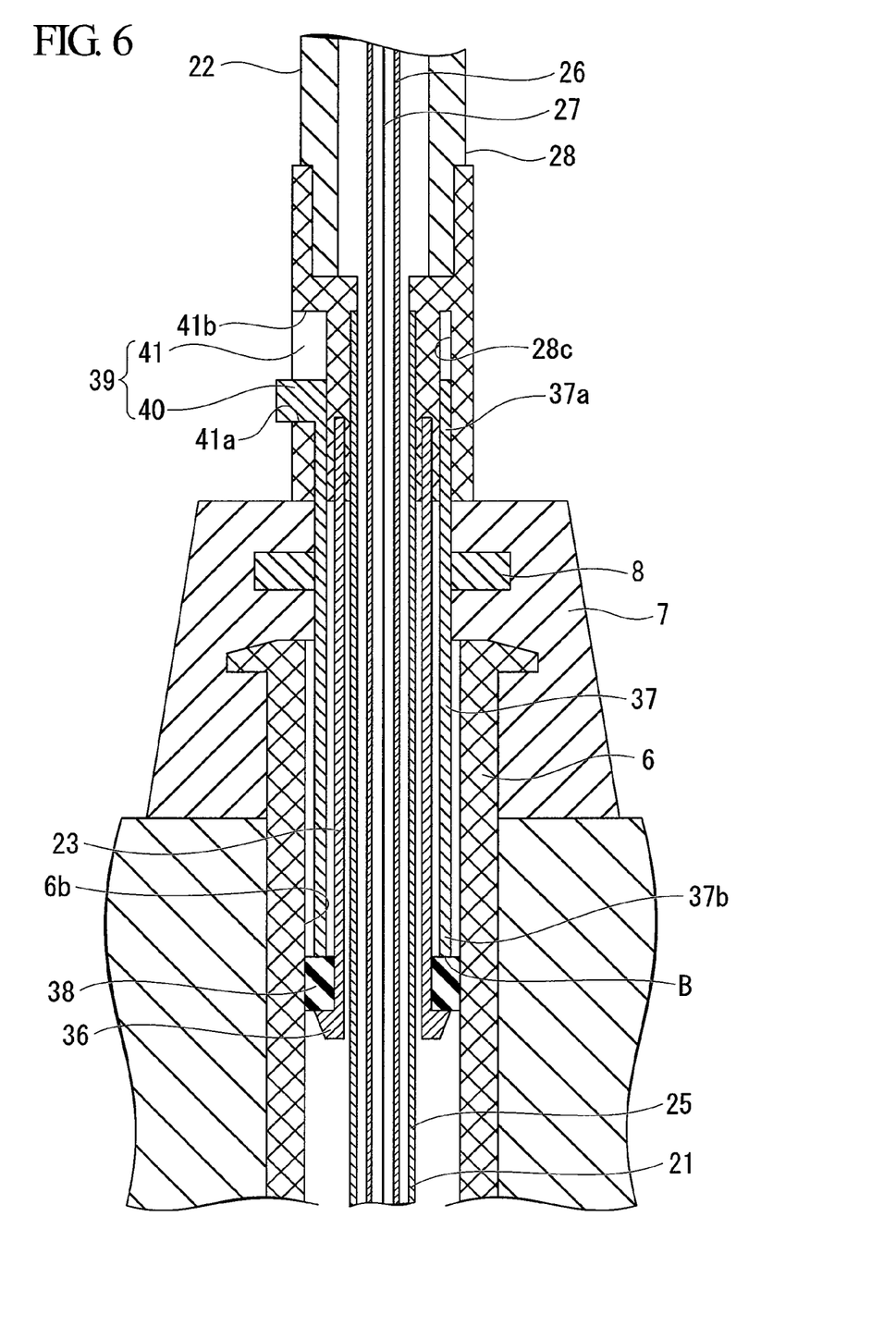
FIG. 6 is an enlarged cross-sectional view of the base-end portion of the insertion section of the puncture needle for an endoscope of the first embodiment of the invention.

The pressing member 37 thereby advances to the distal-end side in the axial direction from the retracted position A to the fixed position B to be engaged at the fixed position B as shown in FIG. 6.

At the fixed position B, the distal-end portion 37b of the pressing member 37 presses the elastic member 38, the elastic member 38 that is sandwiched between the pressing member 37 and the locking section 36 of the guide member 23 thereby elastically contracts in the axial direction.

The elastic member 38 thereby deforms in the radial direction, but since the elastic member 38 is constricted on the inner circumferential side in the radial direction by the hard guide member 23, the elastic member 38 bulges elastically distally from the axial direction and in the radial direction.

Then, the elastic member 38 presses an inner wall 6b of the mouth ring 6, and firmly attaches between the inner wall 6b of the mouth ring 6 and the guide member 23, so that friction occurs.

For this reason, movement of the guide member 23 in the radial direction and movement in the axial direction are restricted, and the guide member 23 is fixed to the inner wall 6b of the mouth ring 6.

In this way, by fixing the guide member 23 to the mouth ring 6, the operation section 22 to which the guide member 23 is fixed, and the insertion section 21 that is fixed to the operation section 22 and inserted inside of the channel 5 are fixed to the ultrasonic endoscope 1.

Next, to sample cells or tissue of a predetermined region in the body, as shown in FIG. 2 or FIG. 3, while confirming the predetermined region with the optical observation section and the ultrasonic observation section, the slider 29 of the operation section 22 is operated, and the distal-end portion 26a of the needle tube 26 is accurately advanced to the predetermined region.

Next, after removing the stylet mouthpiece member 35 to draw out the stylet 27, a suction device not illustrated is connected to the suction mouthpiece member 29b of the slider 29. Then, the suction device suctions the predetermined region where the distal-end portion 26a is positioned via the needle tube 26.

Also, by finely moving the distal-end portion 26a of the needle tube 26 back and forth with the slider 29, cells or tissue of a predetermined region at the distal-end portion 26a are suctioned from the needle tube 26.

Here, the puncture needle 20 is fixed to the endoscope 1 with the forceps plug 7 attached by the pressing member 37 and the elastic member 38 of the fixing section 24.

For this reason, as shown in FIG. 1, the operator is capable of firmly grabbing the ultrasonic endoscope 1 with one hand, accurately moving the slider 29 of the operation section 22 of the puncture needle 20 back and forth with the other hand, and reliably taking samples of cells and tissue at the predetermined region.

Moreover, when mounting the insertion section 21 of the puncture needle 20 by insertion in the ultrasonic endoscope 1 and removing by pulling out therefrom, the insertion opening 5a of the channel 5 is not opened.

For this reason, it is possible to prevent bodily fluids and the like from flowing backwards due to an air-pressure difference occurring between the inside of the body and inside of the channel 5 and the exterior space.

Figure 7:
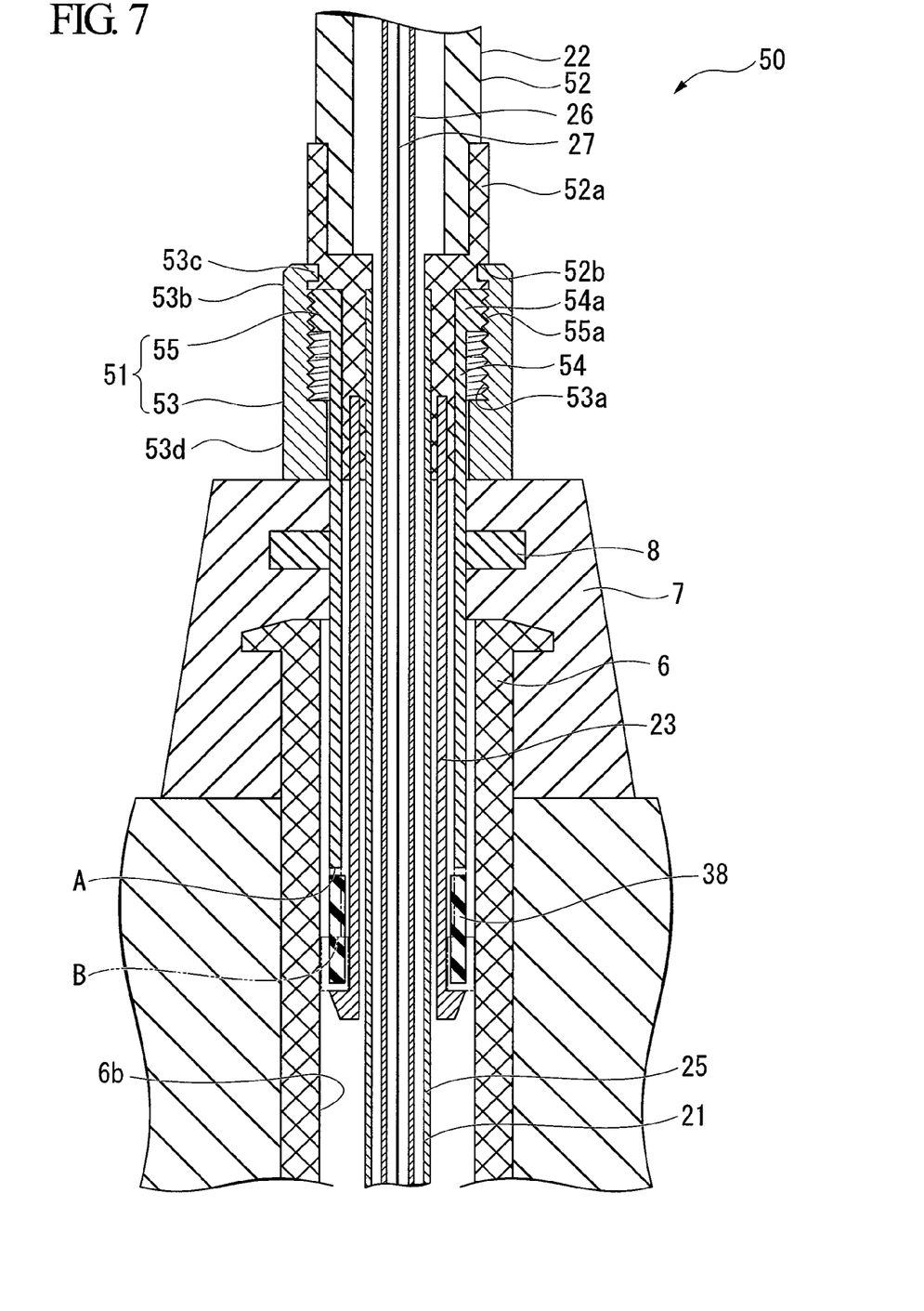
FIG. 7 is an enlarged cross-sectional view of the base-end portion of the insertion section of the puncture needle for an endoscope of a first modified example of the first embodiment of the invention.

FIG. 7 shows a first modified example of the first embodiment.

As shown in FIG. 7, a puncture needle 50 for the endoscope of this modified example is provided with an adjustment ring 53 and a locking projection portion 55 as a positioning mechanism 51.

The adjustment ring 53 is externally fitted around a connection member 52a of an operation section body 52.

The locking projection portion 55 projects distally from the axial direction and in the radial direction at a base-end portion 54a of a pressing member 54.

Also, a female thread 53a is formed on the inner circumferential side of the adjustment ring 53.

Moreover, at the base-end portion 53b of the adjustment ring 53, a projection portion 53c which annularly projects to the inner circumferential side is formed.

An annular groove 52b that corresponds to the projection portion 53c of the adjustment ring 53 is formed on the outer circumferential surface of the connection member 52a of the operation section body 52.

The projection portion 53c of the adjustment ring 53 is rotatably fitted in the annular groove 52b.

Also, a male thread 55a is formed on the outer circumferential surface of the locking projection portion 55 of the pressing member 54.

The male thread 55a screws into the female thread 53a of the adjustment ring 53.

That is, by rotating the adjustment ring 53, it is possible to move the pressing member 54 back and forth. Then, by disposing the locking projection portion 55 at the base-end portion 53b of the adjustment ring 53, the pressing member 54 is positioned at the retracted position A, and enters a state of not pressing the elastic member 38.

Also, by disposing the locking projection portion 55 at the distal-end portion 53d of the adjustment ring 53, the pressing member 54 is locked at a fixed position B and presses the elastic member 38, and it is possible to fix the guide member 23 to the inner wall of the mouth ring 6.

Also, by rotating the adjustment ring 53 in this positioning mechanism 51, it is possible to finely adjust the position of the pressing member 54, and adjust the force of pressing the inner wall 6b of the mouth ring 6 with the elastic member 38.

Figure 8:
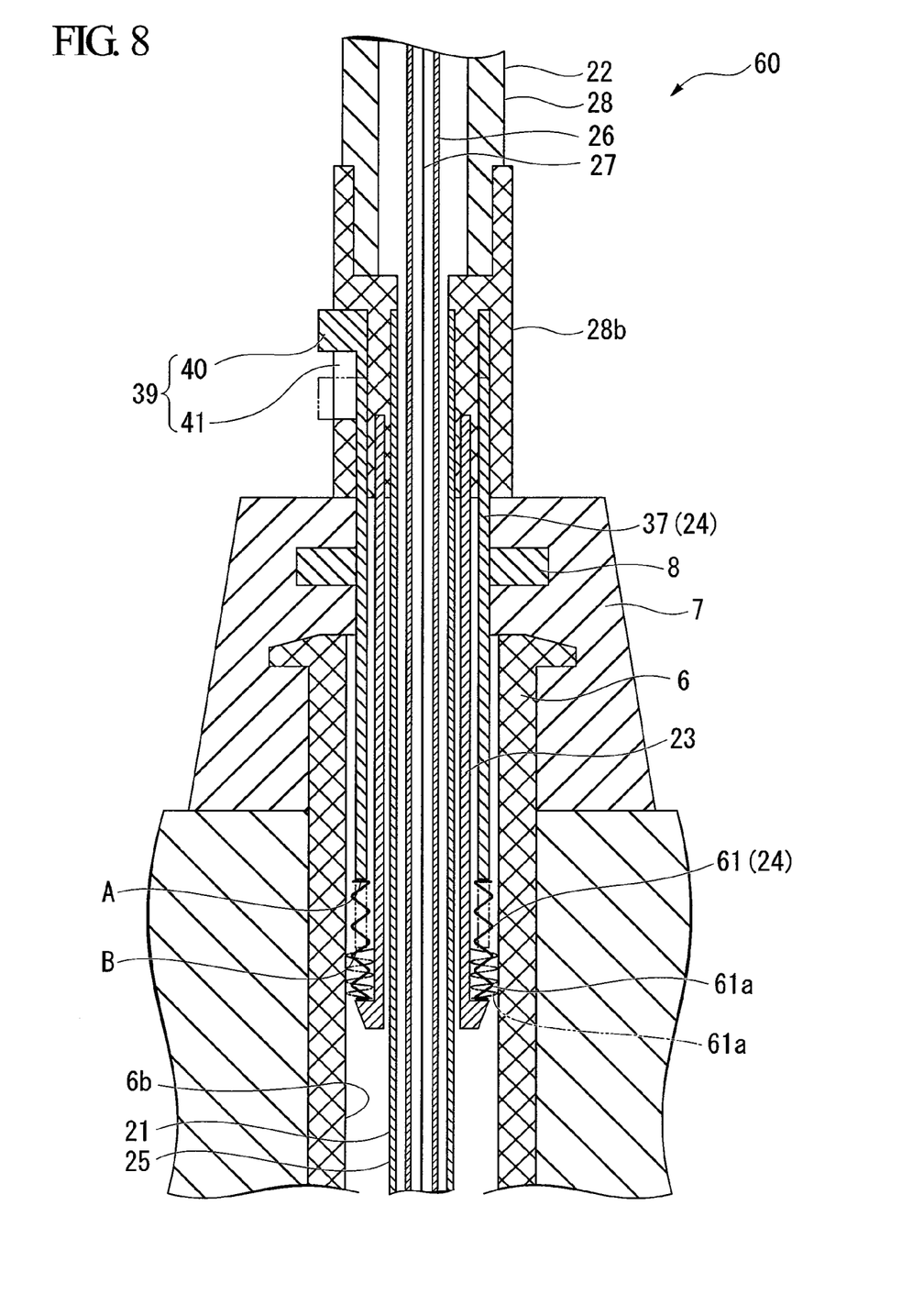
FIG. 8 is an enlarged cross-sectional view of the base-end portion of the insertion section of the puncture needle for an endoscope of a second modified example of the first embodiment of the invention.

FIG. 8 shows a second modified example of the first embodiment.

As shown in FIG. 8, a puncture needle 60 for the endoscope of this modified example is provided with a spring member 61 having a substantially tubular shape and formed in a bellows shape as a fixing member of the fixing section 24.

For this reason, by moving the pressing member 37 back and forth from the retracted position A to the fixed position B, it is possible to elastically expand and contract the spring member 61.

Also, by disposing the pressing member 37 at the fixed position B, mountain portions 61a on the outer circumferential side of the spring member 61 press the inner wall 6b of the mouth ring 6, and it is possible to fix the guide member 23 to the inner wall 6b of the mouth ring 6.

Second Embodiment

Figure 9:
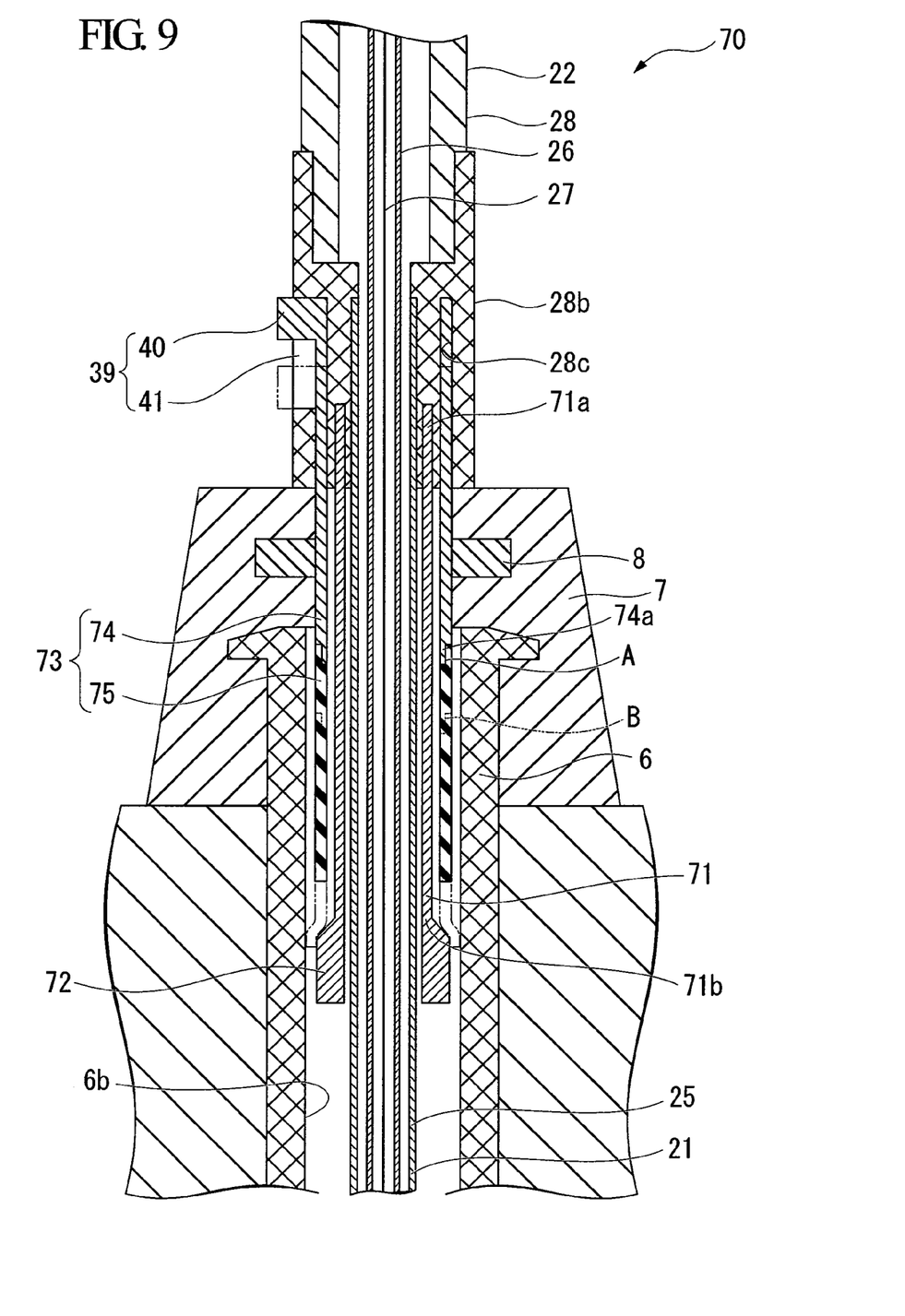
FIG. 9 is an enlarged cross-sectional view of the base-end portion of the insertion section of the puncture needle for an endoscope of a second embodiment of the invention.

FIG. 9 shows a second embodiment of the invention.

In this embodiment, members which are the same as those of the previous embodiment are designated by the same reference numerals, and a description of such components will be omitted.

As shown in FIG. 9, a guide member 71 of a puncture needle 70 for the endoscope of this embodiment has a substantially tubular shape, is fixed to a connection member 28b at a base-end portion 71a, and is externally fitted around the insertion section 21.

A tapered section 72 whose diameter expands from the base-end side to the distal-end side is formed at the distal-end portion 71b of the guide member 71.

The guide member 71 is made of a rigid material.

Also, a fixing section 73 of the puncture needle 70 includes a pressing member 74 having a substantially tubular shape and an elastic member 75 that is a fixing member with a substantially tubular shape.

The pressing member 74 is fitted in a fitting groove 28c of the connection member 28b to be capable of moving back and forth in the axial direction and is externally fitted around the guide member 71.

The elastic member 75 is fixed to a distal-end portion 74a of the pressing member 74, and externally fitted around the guide member 71.

The pressing member 74 is made of a rigid material.

The elastic member 75 is formed with rubber, silicone resin, and the like to be capable of elastic deformation.

That is, the elastic member 75 is capable of moving back and forth with the pressing member 74.

Accordingly, when the pressing member 74 advances to the fixed position B, the elastic member 75 is disposed at the tapered section 72 of the guide member 71.

The elastic member 75, following the shape of the tapered section 72, elastically expands in diameter to press the inner wall 6b of the mouth ring 6.

For this reason, the elastic member 75 is firmly attached between the inner wall 6b of the mouth ring 6 and the tapered section 72 of the guide member 71, and due to the friction that occurs from this attachment, the guide member 71 is fixed to the inner wall 6b of the mouth ring 6.

If the pressing member 74 is retracted to the retracted position A, the elastic member 75 contracts in diameter. It is thereby possible to release the fixation of the guide member 71.

The pressing member 74 and the elastic member 75 may be constituted by an integrated structure, if the pressing member 74 and the elastic member 75 are capable of moving back and forth between the retracted position A and the fixed position B without undergoing buckling distortion, and if the material of portion that is disposed at the tapered section 72 is capable of elastic deformation following the shape of the tapered section 72.

Third Embodiment

Figure 10:
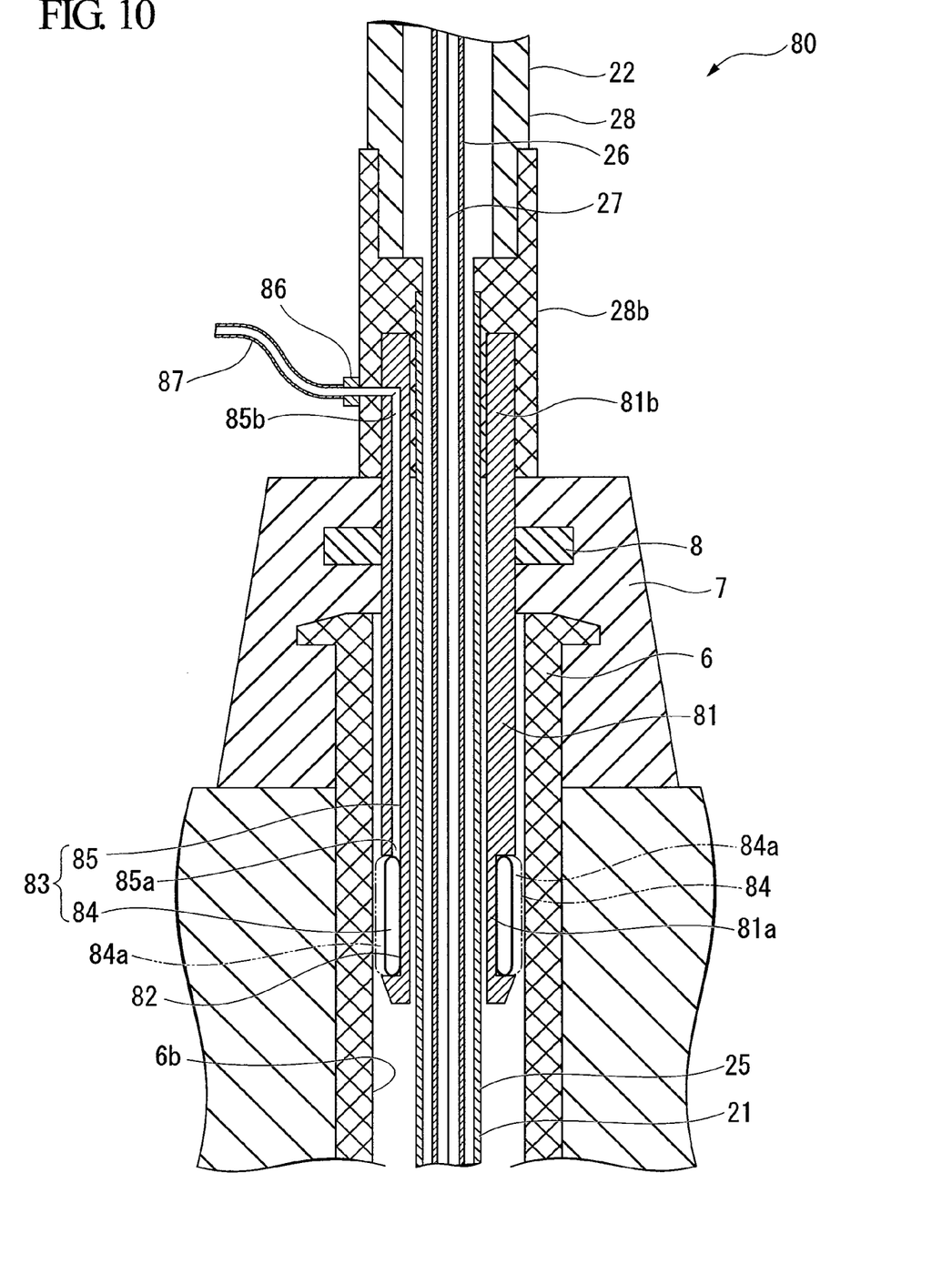
FIG. 10 is an enlarged cross-sectional view of the base-end portion of the insertion section of the puncture needle for an endoscope of a third embodiment of the invention.

FIG. 10 shows a third embodiment of the invention.

In this embodiment, members which are the same as those of the previous embodiment are designated by the same reference numerals, and a description of such components will be omitted.

As shown in FIG. 10, a guide member 81 of a puncture needle 80 for the endoscope of this embodiment has a substantially tubular shape, is fixed to the operation section body 28 at the base-end portion 81b, and is externally fitted around the insertion section 21.

Also, a housing groove 82 is annularly formed on the outer circumference side of the distal-end portion 81a.

The guide member 81 is made of a rigid material.

Also, the puncture needle 80 for the endoscope is provided with an annular tube body 84 that is a fixing member and a pipe 85 that is formed inside of the guide member 81, together serving as a fixing section 83.

The pipe 85 is, at the distal-end portion 85a, in communication with an inner portion 84a of the tube body 84, and, at the base-end portion 85b, is connected with a connection valve 86 provided at the operation section body 28.

For this reason, by connecting an air-intake-and-flue-ventilation pipe 87 that is in communication with an air-intake-and-flue-ventilation device which is not illustrated to the connection valve 86 and supplying air, it is possible to expand the tube body 84 via the pipe 85, and thus cause the tube body 84 to deform distally from the axial direction and in the radial direction.

The expanded tube body 84 presses the inner wall 6b of the mouth ring 6, and thus is firmly attached between that and the guide member 81.

It is thereby possible to fix the guide member 81 to the inner wall 6b of the mouth ring 6.

The tube body 84 was expanded by supplying air with the air-intake-and-flue-ventilation device, but it is also possible to inject a liquid.

Fourth Embodiment

Figure 11:
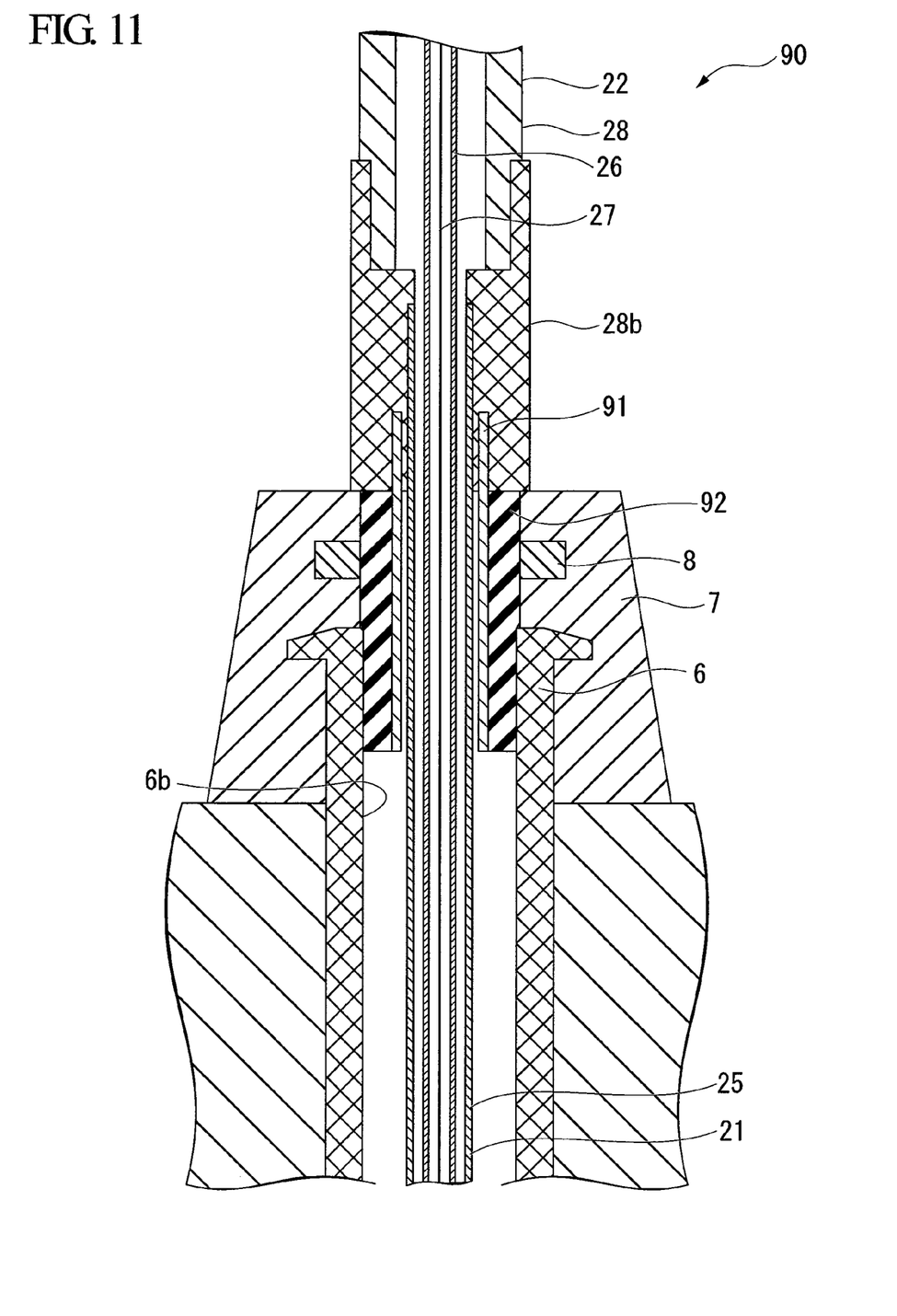
FIG. 11 is an enlarged cross-sectional view of the base-end portion of the insertion section of the puncture needle for an endoscope of a fourth embodiment of the invention.

FIG. 11 shows a fourth embodiment of the invention.

In this embodiment, members which are the same as those of the previous embodiment are designated by the same reference numerals, and a description of such components will be omitted.

As shown in FIG. 11, a puncture needle 90 for the endoscope of this embodiment includes a guide member 91 that has a substantially tubular shape and is externally fitted around the insertion section 21, and an elastic member 92 that is externally fitted around the guide member 91.

The guide member 91 and the elastic member 92 are both fixed to the operation section body 28.

Also, the guide member 91 is made of a rigid material.

The elastic member 92 is formed with rubber, silicone resin, and the like to be capable of elastic deformation. The outer diameter of the elastic member 92 is set to be slightly larger than the inner diameter of the mouth ring 6.

For this reason, if the insertion section 21 of the puncture needle 90 is inserted from the mouth ring 6 to the channel, the elastic member 92 elastically deforms in the radial direction to conform to the inner diameter of the mouth ring 6, and by contracting in diameter, enters the mouth ring 6.

Since a restoring force acts at the outer side in the radial direction of the elastic member 92, the inner wall 6b of the mouth ring 6 is pressed by this, and the elastic member 92 comes to be firmly attached between the guide member 91 and the inner wall 6b.

It is thereby possible to fix the guide member 91 to the inner wall 6b of the mouth ring 6.

In this embodiment, the elastic member 92 is made to elastically deform in conformance with being inserted in the mouth ring 6 and press the inner wall 6b of a mouth ring 6, but is not limited thereto.

It is possible to set the outer diameter of the elastic member 92 to be substantially equal to the inner diameter of the mouth ring 6. Inserting in the mouth ring 6 by force thereby generates friction with the inner wall 6b of a mouth ring 6, enabling restriction of movement of the guide member 23 in the radial direction and movement in the axial direction so that it is fixed.

Also, the guide member 91 and the elastic member 92 may be constituted by an integrated structure, if the materials of the guide member 91 and the elastic member 92 are capable of deforming and do not press the insertion section when inserted in the channel.

Embodiments of the invention have been described in detail with reference to the drawings, but these are exemplary of the invention and are not to be considered as limiting. Design modifications are included within the scope of not departing from the spirit or scope of the invention.

In the above embodiments, an ultrasonic endoscope was given as an example of an endoscope, but is not limited thereto, and it is possible to use any one provided it is an endoscope that has a channel that allows insertion of a treatment tool for an endoscope.

Also, a puncture needle for an endoscope was given as an example of a treatment tool for an endoscope, but is not limited thereto.

Provided it is a treatment tool for an endoscope that is used by being inserted in the channel of an endoscope, by using a guide member and a fixing section, it is possible to use by fixing to the endoscope.

Moreover, the treatment tool for an endoscope is one that is fixed by the fixing member of the fixing section pressing the inner wall of the mouth ring, but it may also be fixed by pressing the inner wall of the channel that is in communication from the mouth ring.

According to the treatment tool for an endoscope of the invention, when inserting the insertion section inside the channel of an endoscope, the fixing section is firmly attaches in a space between the inner wall of the mouth ring or the channel and the guide member, and the guide member is fixed to the inner wall of the mouth ring or the channel by the friction that occurs.

The operation section that is fixed to the guide member, and the insertion section that is fixed to the operation section can be thereby fixed to the endoscope.

That is, in the state of a forceps plug mounted to the mouth ring, it is possible to insert the insertion section as well as the guide member and the fixing section that are externally fitted around the insertion section inside the channel of the endoscope and fix the operation section and the insertion section to the endoscope.

According to the treatment tool for an endoscope of the invention, the insertion section, the guide member, and the fixing section are inserted inside of the channel of the endoscope.

Then, following the insertion, the fixing member of the fixing section is caused to deform, pressing the inner wall of the mouth ring or the channel. The fixing member is thereby firmly attached between the inner wall of the mouth ring or the channel and the guide member, and the guide member is fixed.

For this reason, it is possible to readily perform insertion, and due to the deformation of the fixing member in the radial direction after insertion, it is possible to effectively generate friction and fix it.

According to the abovementioned treatment tool for an endoscope of the invention, the pressing section advances and presses the fixing member. The distal-end side of the fixing member is thereby bound by the locking section, the base-end side of the fixing member is bound by the pressing member, and the inner circumferential side of the fixing member is bound by the guide member.

The fixing member thereby elastically deforms distally from the axial direction and in the radial direction.

Then, the fixing member presses the inner wall of the mouth ring or the channel of the outer circumferential side, the fixing member thereby comes into firm contact with the guide member between the inner wall and the guide member, and the guide member is fixed.

By retracting the pressing member, the elastic deformation of the fixing member is released, and a state arises of not pressing the inner wall of the mouth ring or the channel.

It is thereby easy to insert the insertion section into the channel of the endoscope and easy to remove it.

According to the treatment tool for an endoscope of the invention, the pressing section advances. The fixing member that is fixed to the distal-end portion is thereby disposed at the tapered section of the guide member, and elastically expands in diameter.

Then, the fixing member presses the inner wall of the mouth ring or the channel of the outer circumferential side, the guide member thereby comes into firm contact with the guide member between the inner wall and the guide member, and the guide member is fixed.

By retracting the pressing member, the fixing member also retracts and contracts in diameter, and a state arises of not pressing the inner wall of the mouth ring or channel. It is thereby easy to insert the insertion section into the channel of the endoscope and easy to remove it.

According to the treatment tool for an endoscope of the invention, after insertion of the insertion section in the channel of the endoscope, the positioning mechanism can dispose and lock the pressing member at a fixing position that presses the fixing member and causes it to deform in the radial direction.

For this reason, it is possible to readily switch between a state of being capable of inserting the insertion section inside the channel and a state of the insertion section and the operation section being fixed in the endoscope. Also, it is possible to reliably maintain the state of being fixed in the endoscope.

According to the treatment tool for an endoscope of the invention, it is possible to put the operation section and the insertion section in a state of being fixed to the endoscope with the fixing section.

For this reason, it is possible to grasp the endoscope to which the operation section and the insertion section are fixed by one hand, and operate the slider of the operation section with the other hand.

Accordingly, it is possible to accurately move the needle tube and stylet back and forth in a predetermined region in the body, and take samples of cells and tissue at the predetermined region.

The treatment tool for an endoscope of the invention is provided with a guide member and a fixing member.

The fixing section fixes the guide member to the inner wall of the mouth ring or the channel. It is thereby possible to fix the operation section and the insertion section to the endoscope with the forceps plug mounted.

For this reason, the operability of the operation section is favorable, and it is possible to prevent backflow of bodily fluids during attachment/detachment.

What is claimed is:

1. A treatment tool for an endoscope comprising:
an insertion section which is capable of being inserted from an opening for insertion of the treatment tool, the opening being provided at a proximal-end portion of a channel of the endoscope to an inside of the channel, the opening having a mouth ring which communicates with the channel and a plug which is fitted together with the mouth ring, and the insertion section being capable of being inserted from the mouth ring to the inside of the channel via the plug;
an operation section provided at a proximal end of the insertion section;
a connecting member provided at a distal end of the operation section, the connecting member being capable of attaching to the plug depending on an insertion of the insertion section to the inside of the channel;
a guide member that has a tubular shape, that is externally fitted around the insertion section at the proximal end of the insertion section that is connected to the connecting member, and that is rigid; and a fixing section provided at a distal portion of the guide member, the fixing section being located in the mouth ring when the connecting member is attached to the plug, the fixing section being capable of fixing the guide member to the mouth ring by fitting to an inner wall of the mouth ring due to an expansion of the fixing section toward an outside of the fixing section, wherein;

the insertion section and the operation section are capable of being fixed to the endoscope by an attaching of the connecting member to the plug and a fixing of the fixing section to the mouth ring, the fixing section includes:
- a fixing member having an elastic body that is expandable toward an outside thereof;
- a pressing member which is capable of pressing the fixing member in an axial direction of the fixing member; and
- a locking section which is placed at a distal portion of the guide member, and the fixing member is sandwiched between the pressing member and the locking section to thereby elastically contract in the axial direction of the fixing member, and the fixing member is capable of fixing the mouth ring by pressing an inner surface of the mouth ring by expanding toward the outside thereof in the mouth ring in accordance with the pressing by pressing member.

2. The treatment tool for an endoscope according to claim 1, wherein
the insertion section includes:
a sheath that has flexibility;
a needle tube with a tubular shape that is inserted inside the sheath and having a distal-end portion that is sharpened; and
a stylet that is passed through the needle tube, and wherein the operation section has a slider that is capable of moving the needle tube and the stylet back and forth in an axial direction of the sheath relative to the sheath.

3. The treatment tool for an endoscope according to claim 1, wherein
the fixing member consists of an elastic body that is externally fitted around the guide member.

* * * * *